United States Patent [19]

Torti et al.

[11] Patent Number: 5,061,449
[45] Date of Patent: * Oct. 29, 1991

[54] EXPANDABLE MULTI-CHANNEL PIPETTER

[75] Inventors: Victor A. Torti, Brookline; Gary E. Nelson, Hollis, both of N.H.; Laurence Keene, Brookline, Mass.; George P. Kalmakis, Reading, Mass.

[73] Assignee: Matrix Technologies, Corp., Lowell, Mass.

[ * ] Notice: The portion of the term of this patent subsequent to Oct. 15, 2008 has been disclaimed.

[21] Appl. No.: 385,234

[22] Filed: Jul. 25, 1989

[51] Int. Cl.⁵ .................................................. B01L 3/02
[52] U.S. Cl. ...................................... 422/100; 422/65; 422/104; 436/180; 73/863.32; 73/864.14
[58] Field of Search .................... 422/100, 99, 65, 104; 436/180; 73/863.32, 864.14, 864.16, 864.17

[56] References Cited

U.S. PATENT DOCUMENTS

| 4,599,220 | 7/1986 | Yonkers et al. | 73/864.17 X |
| 4,779,467 | 10/1988 | Rainin et al. | 422/100 X |
| 4,824,642 | 4/1989 | Lyman et al. | 422/100 |
| 4,830,832 | 5/1989 | Arpagaus et al. | 422/65 |

Primary Examiner—Robert J. Warden
Assistant Examiner—Lynn M Kummert
Attorney, Agent, or Firm—Wolf, Greenfield & Sacks

[57] ABSTRACT

A pipetting system having a plurality of fittings whose spacing can be simultaneously expanded from one dimension to another. Increasing the spacing is accomplished by pulling a rod, attached to one fitting, which elongates the series of fittings to a second position. In addition, there is a release mechanism for removing disposable tips attached to the fittings. The release mechanism can be operated in either position of the fittings. The mechanism is trigger actuated.

23 Claims, 6 Drawing Sheets

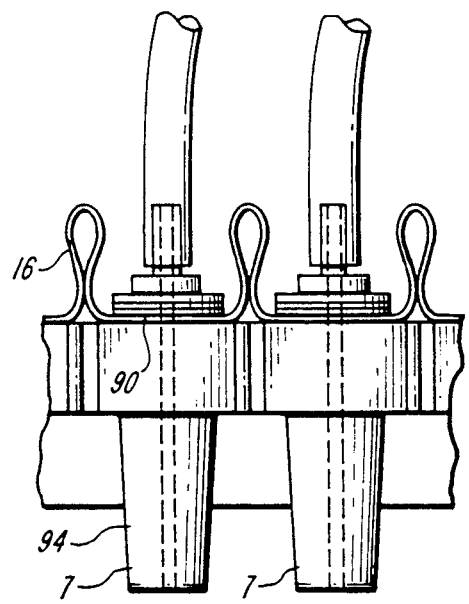
FIG. 2
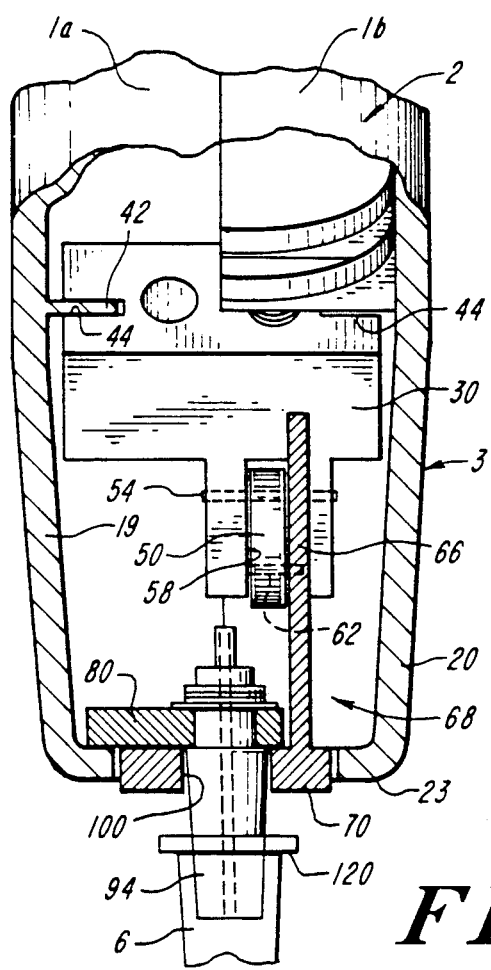
FIG. 4
FIG. 5

EXPANDABLE MULTI-CHANNEL PIPETTER

BACKGROUND OF INVENTION

This invention relates to liquid transfer devices used in laboratories, and more particularly, is directed toward a multi-channel pipetting device which enables the user to adjust the spacings between pipette tips.

Pipetting systems are used in laboratories for the transfer of relatively small quantities of liquids. The liquid is normally drawn into the tips by suction and is subseguently released into the wells of microtiter plates or other receptacles. Frequently the transfer involves patient samples which are moved from one set of receptacles to another of different spacing. Because virtually all hand operated multi-channel pipettes have a fixed spacing between pipette tips, the transfer must be made by single channel pipettes, which is a slow and very inefficient process. Some large laboratories and pharmaceutical firms which perform thousands o transfers a day have purchased fully automatic robotic systems that cost tens or hundreds of thousands of dollars, but those systems are beyond the reach of small and medium size firms.

One important object of this invention is to provide a pipetting system which is relatively inexpensive but which is capable of being adjusted to vary the spacing between the pipette tips so that liquid may be transferred from one set of receptacles to another set of different spacing.

A more specific object of the present invention is to provide a pipetting system that enables the user with a simple manipulation to move the pipette tips from one set of spacings to another.

It is a further object of the present invention to provide a pipetting system which allows the fittings that carry the pipette tips to be adjusted simultaneously between two standard spacings of the receptacles.

Another important object of the present invention is to provide a hand-held expandable pipetter that can easily be customized during manufacturing to establish two preselected settings for the fittings of the pipetter, which support the pipette tips.

It is a further object of the present invention to provide a pipetting system that is of simple construction and therefore relatively inexpensive to manufacture.

It is a further object of this invention to provide a pipetting system that is easy to operate and does not require complicated adjustments for use.

It is a further object of the present invention to provide a hand-held pipetter having a tip removing assembly that remove tips safely and efficiently regardless of the positions of the tips and their fittings on the pipetter.

It is a further object of the present invention to provide a pipetting system having a tip removing assembly that requires a minimum force to remove the tips.

The system is embodied in a boot-shaped instrument having a housing with a handle section and a foot or lower section. A plurality of fittings aligned in a row extend downwardly from the foot, and a manually operated mechanism within the foot is attached to the fittings to enable a user to vary the spacing between them. The mechanism includes a rod attached to the fitting at one end of the row, and all the fittings are attached to on another by a flexible strap. The rod extends out of the foot and carries a knob to facilitate its actuation. By moving the rod between its extreme positions the row of fittings are moved between contracted and expanded positions established by the length of the strap and the mountings that slidably carry the fittings on the foot.

A tip removing mechanism operated by a trigger on the handle section has a stripper that can remove the disposable tips from the fittings regardless of the spacing of the fittings. As the trigger is squeezed, the stripper pushes the tips off the fittings. In order to reduce the overall force required to eject the tips the ejecting surface of the stripper is stepped so that groups of tips are engaged in sequence causing first one group and then another to be pushed off the fittings.

The many objects and features of this invention will be better understood and appreciated from the following detailed description of the preferred embodiment thereof read in connection with the accompanying drawings.

BRIEF FIGURE DESCRIPTION

FIG. 2 is an enlarged, fragmentary, cross-sectional view of the pipetter fittings and tips in the position of FIG. 1;

FIG. 4 is a cross-sectional view taken along the section line 4—4 in FIG. 3;

FIG. 5 is a vertical cross-sectional view of the pipetter taken along the section line 5—5 in FIG. 3;

DETAILED DESCRIPTION OF THE PREFERRED EMBODIMENT

Figure 1:
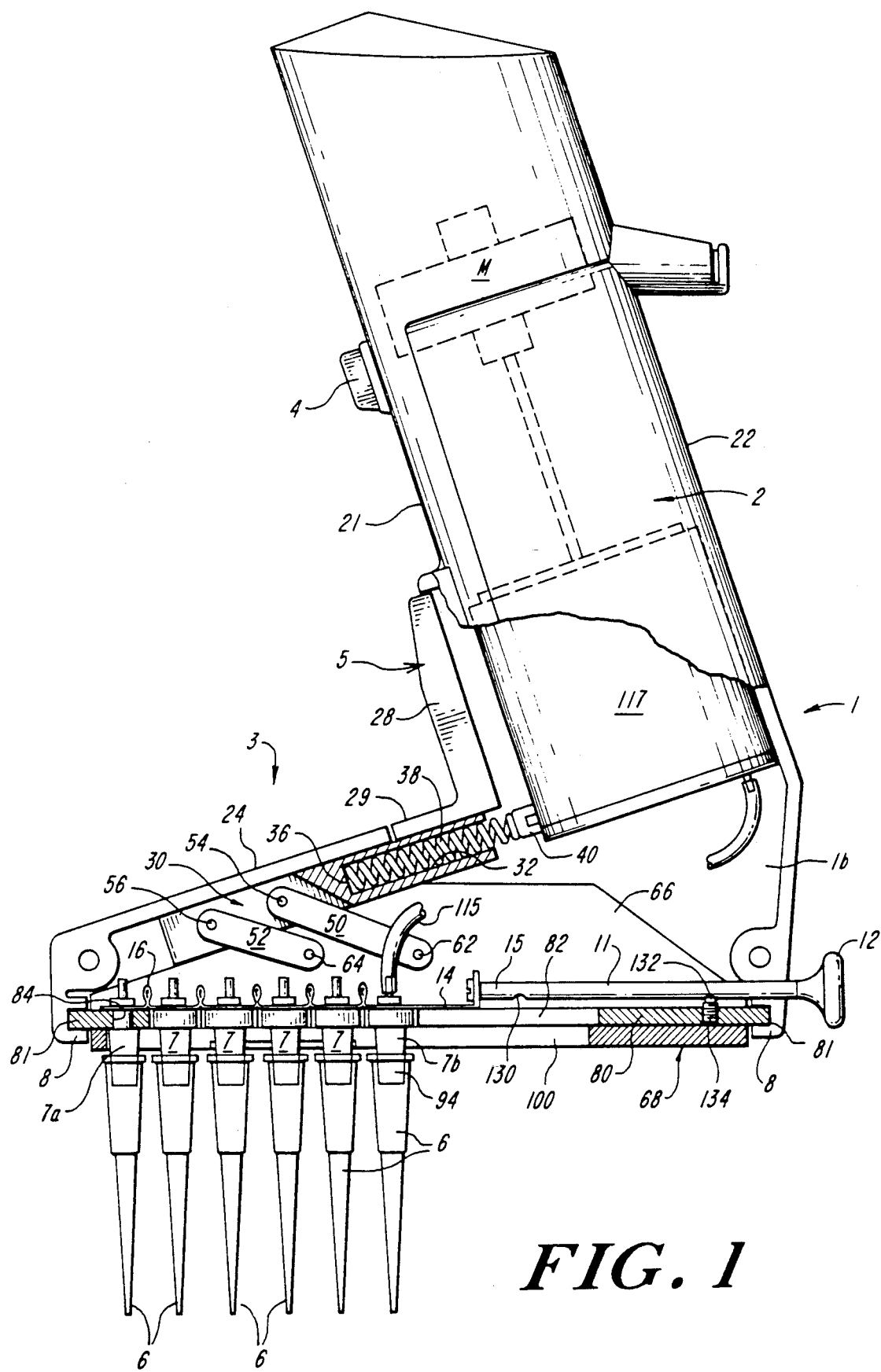
FIG. 1 is a cross-sectional side view of a multi-channel pipetter constructed in accordance with this invention and showing the pipetter tips and fittings in the closely spaced position.

Referring now to the drawings, the pipetter of the present invention has a boot-shaped housing 1 consisting of a handle section 2 and a lower or foot section 3. The handle section 2 carries both a push button 4 for initiating the pipetting action and a trigger 5 for removing disposable tips 6 which are frictionally secured to tip fittings 7 that project from the bottom 8 of the lower housing section 3. An actuating rod 11 carrying a knob 12 projects rearwardly from the lower section 3 and is secured at its forward end 15 within the housing 1 to an L-shaped bracket 14. The L-shaped bracket 14 in turn is connected to the rear most fitting 7b, and the several fittings 7 are connected together by a flexible strap 16. By pushing and pulling the knob 12 and rod 11 the fittings are moved between the positions of FIGS. 1 and 3. The details of the mechanisms for removing the tips 6 and for varying the spacing of the fittings 7 are described more fully below.

The housing 1 of the pipetting system is made up of a pair of mating half shells 1a and 1b (see FIG. 5) which together form the handle section 2 and foot or lower section 3. The shells 1a and 1b include sidewalls 19 and 20 and front and back walls 21 and 22 that together define the handle section 2 and the lower section 3. The front, back and bottom of the lower section 3 are enclosed by the walls 21, 22 and 23, while the top of the bottom section forward of the handle is closed by wall 24.

An elongated aperture 25 is provided in the bottom wall 23 and extends substantially the full length thereof symmetrical with respect to the parting line 26 that joins the two shells. The push button 4 which extends forwardly from the front edge of the handle section 2 is normally at the height of one's second finger when the handle is engaged while the trigger 5 which also extends forwardly from the front wall of the handle is at the height of the 4th and 5th fingers. The trigger is generally L-shaped having an upwardly extending section 28 along the front of the handle section 2 and base 29 which slides along the top wall 24 of the bottom section 3.

Figure 3:
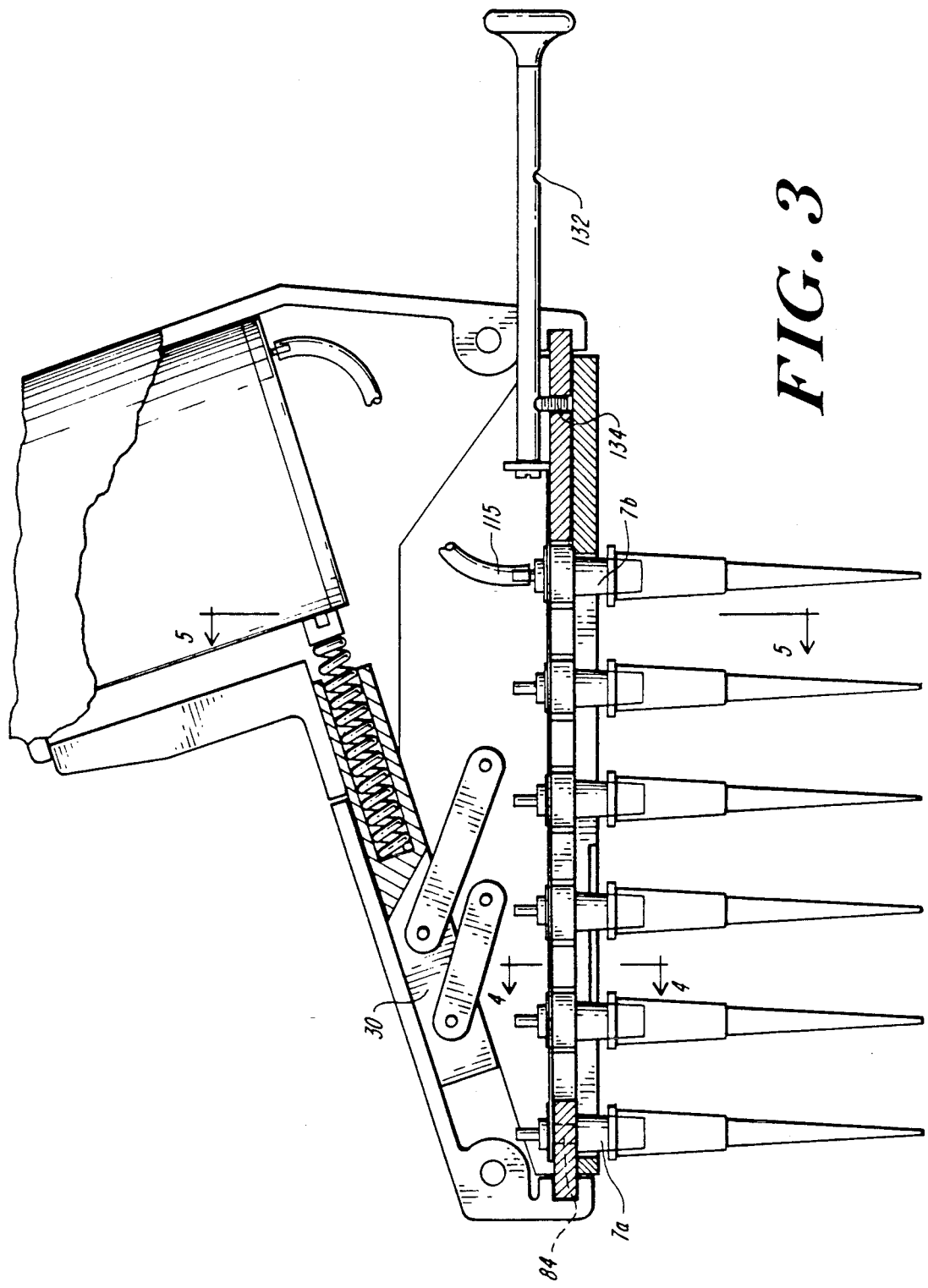
FIG. 3 is a fragmentary cross sectional view similar to FIG. 1 but showing the fittings and tips in the widely spaced or expanded position.

The details of the pipetting system for drawing liquid in metered volumes into the tips 6 and for expelling the liquid from the tips is not part of the present invention and therefore is described only briefly herein. The system includes a cylinder 117 in the handle section 2 housing a plurality of parallel cylindrical chambers (not shown) that correspond in number to the number of fittings 7. In the embodiment shown, six fittings are included, but it should be appreciated that the number may vary. A piston (not shown) is slidably mounted in each chamber, and the pistons in turn are moved in tandem by a suitable electric motor M disposed in the handle section 2 above the cylinder 117. Each chamber is connected to one fitting 7 by a duct 115, only one of which is shown in FIGS. 1 and 3. Movement of the pistons by the motor M in one direction in their respective chambers draws liquid into the tips 6, and movement in the other direction expels the liquid from them. The motor in turn may be automatically controlled so as to program the volume of liquid drawn into and expelled from the tips during each actuation of the button 4 in the motor circuit. The button 4 is connected in the motor circuit to afford the operator control of the pipetting operation.

The trigger 5 is integrally molded with a slide 30 that is disposed in the bottom section 3 of the housing immediately beneath top wall 24. The slide 30 has a recess 32 open to the rear and closed at its front end as shown at 36. A coil spring 38 is disposed in the recess 32 and bears against the end wall 36 at its front and against a barrier 40 carried in the rear of the half shell 1b of the housing. The slide 30 is carried by a pair of flanges 42 (one shown in FIG. 5) provided on each half shell of the housing and which are disposed in slots 44 in the side edges of the slide. The spring 38 urges the slide in a forward direction toward the front wall or toe 24 of the lower section of the housing, but the spring may be overridden by squeezing the trigger 5, which will compress the spring and draw the slide in the direction of rear wall 22 to the position of FIG. 6. When the trigger is released, the slide returns to the position shown in FIG. 1.

A pair of parallel links 50 and 52 are pivotally secured to the forward end of the slide 30 by a pair of pivot pins 54 and 56 that extend through holes in the upper ends of the links and which span the slot 58 formed in the slide 30 into which the links extend. The other ends of the links 50 and 52 are connected by means of pivot pins 62 and 64 to the vertical flange 66 of stripper plate 68. As will become apparent below, the stripper plate 68 is confined to vertical translational motion in housing 1, and that motion is imparted to the stripper plate by actuation of slide 30. As the slide 30 is actuated by trigger 5 against the bias of spring 38, the links 50 and 52 acting on the flange 66 urge the stripper plate 68 downwardly to the position shown in FIG. 6 so that its horizontal flange 70 which performs the stripping action will force the tips 6 off the fittings 7. When the trigger 5 is released and the spring 38 forces the slide 30 to move in a forwardly direction, the links 50 and 52 draw the stripper plate upwardly in the housing to the retracted position of FIGS. 1 and 3.

Figure 6:
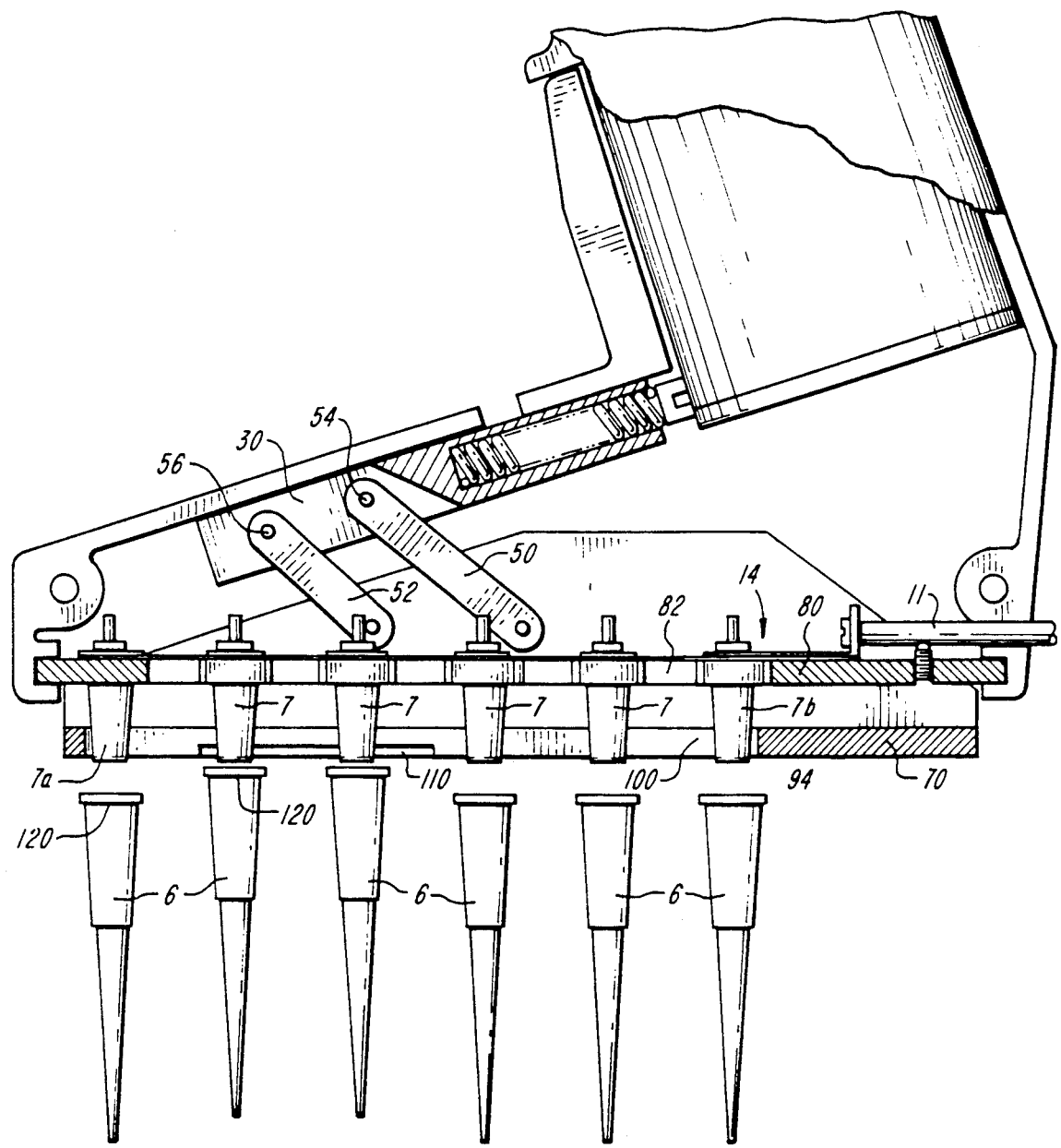
FIG. 6 is a cross-sectional view similar to FIG. 3 but showing how the stripper assembly removes the tips from the fittings.

A tip fitting mounting plate 80 is secured immediately above the bottom wall 23 of the housing by slots 81 formed in each half shell 1a and 1b (see FIGS. 1, 3, and 6). The mounting plate 80 includes an elongated slot 82 narrower and somewhat shorter than the opening 25 in the bottom wall 23. All but one (fitting 7a) of the fittings 7 is slidably mounted in the slot sc that they may be moved toward and away from the front wall 21 by means of the actuating rod 11 and its knob 12. The forward most fitting 7a is disposed in a separate opening 84 in the plate 80 and is immovable. The slot 82 forms a track for the fittings so as to guide their sliding motion to and fro along the bottom wall 23. Each of the fittings disposed in the slot 82 has a truncated cone-shaped stem 94 having a diameter at its upper end which is larger than the width of slot 82, and consequently, the edges of the upper end of the stem bear against the lower surface of the mounting plate 80. Above the stem each fitting (excepting 7a) has a waist 96 which extends through the slot 82. The waist also extends through a hole 90 in the strap 16. A thin retaining plate 92 surrounds the upper end of the fitting above the strap, and the assembly is held together on the mounting plate 80 by a C-shaped clip 93. The upper end of each fitting carries a nipple 98 which in turn is connected to the lower end of duct 115. It will, of course, be appreciated that a passage extends through each fitting from the lower end of the stem 94 to the upper end of nipple 98, which passage is in communication with the duct passage.

The fitting 7a is mounted in its opening 84 in the mounting plate 80 in precisely the same manner described above in connection with the other fittings 7 disposed in the slot 82. The only difference between the mounting of the other fittings and that of fitting 7a is that fitting 7a is rigidly secured in place and cannot move. It should also be noted that the rear most fitting 7b in slot 82 is connected to the bracket 14 in turn connected to the rod 11.

As described above, the horizontal flange 70 of the stripper plate 68 has a slot 100 formed therein through which the stems 94 of the fittings extend. The slot 100 in the flange does not interfere in any way with the sliding motion of the fittings in the mounting plate 80. The slot 100 is, however, narrower than the outer diameter of the upper ends 120 of the tips 6 which are mounted on the stems 94 (see FIGS. 4 and 5). Consequently, when the stripper plate is actuated by squeezing the trigger 5, the horizontal flange 70 moves downwardly toward the lower ends of the stems 94, and the sides engage the upper ends 120 of the tips to push them off the fittings 7.

It will be noted in FIGS. 3, 4, and 6–8 that steps 110 are provided in the sides of the slot 100 in flange 70. As a result, when the trigger 5 is squeezed, those tips 6 which are in the path of the steps 110 in the margin are engaged by the flange after the other tips are engaged by the flange. Consequently, the stripper plate 68 does not simultaneously engage all of the tips but rather their engagement is staggered so that a reduced force is required to eject them. First the tips aligned with the portions of the slot 100 which do not include the stepped edge 110 are are ejected, and thereafter those aligned with the stepped edges are ejected as suggested in FIG. 6.

Figure 7:
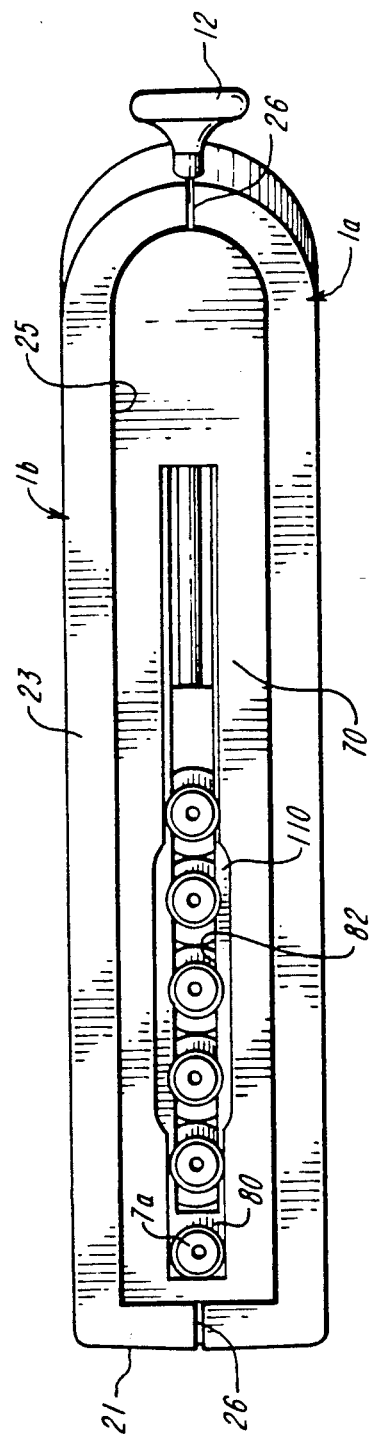
FIG. 7 is a bottom view of the pipetter of FIG. 1 with the fittings in their closely spaced position.
Figure 8:
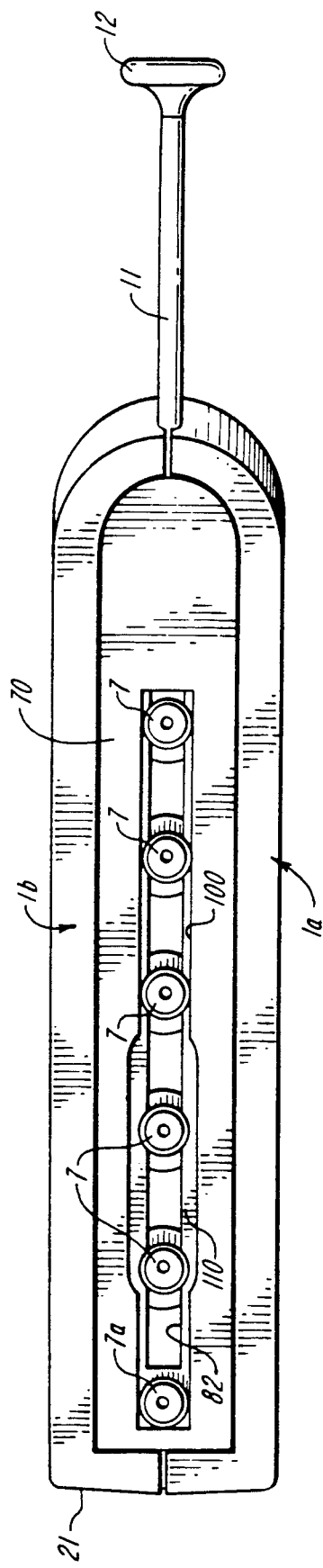
FIG. 8 is a view similar to FIG. 7 but showing the fittings in their widely spaced position.

It will be noted in FIG. 7 wherein the fittings 7 are in their closely spaced relationship three of the fittings ar aligned with the step 110 and three are not. Consequently when the trigger 5 is squeezed initially, the first, second and sixth tips, counting from the left, will be ejected, and then the remaining tips will be ejected. When the fittings are in their maximum spaced relationship, only two of the fittings are aligned with the step 110 and consequently first four of the tips and then the two remaining tips are ejected upon actuation of the stripper 68 by the trigger 5.

It will be appreciated that in the manufacture of the pipetter shown, the maximum spacing of the tips 7 may be varied by using straps 16 of different length and hole spacings. With longer straps and greater spacings, the spread of the fittings will be greater. It may or may not prove desirable when using straps of different length to use mounting plates 80 having slots 82 of different lengths as well. It is essential, however, that the fittings be maintained in parallel relationship so that the tips 6 mounted on them will remain parallel with one another. This is, of course, true whether the pipetter has six or a different number of channels.

It will be appreciated that the tip fittings 7 are designed to slide from side to side in the slotted mounting plate 80, and their attachment to the flexible strap 16 is such that when the strap is pulled taut the tip fittings are set at their expanded spacing. To move the tip fittings to their closer spacing, it is only necessary to push the rod 11 into the housing 1, which causes the waists 96 of the tips 7 to engage one another as in FIGS. 1 and 2. The flexible ducts 115 which connect each of the fitting nipples 98 to the cylinder 117 allow the fittings to move freely on the mounting plate 80 without interference. Furthermore, because the strap 16 is made of a flexible but non-stretchable material, the strap will fold accordion-like as shown in FIG. 2 when the tips are moved to the closely spaced position, and when the fittings are spread apart by means of the rod 11, the strap will be pulled flat and the non-stretchable character of the strap and the slot will limit the fitting separation to a precise dimension.

In order to more positively establish the two positions in which the fittings may be spaced, a pair of notches 130 and 132 may be provided in the rod 11, which cooperate with a ball detent 134. When the detent snaps into notch 130 the user will sense that the closely spaced relationship of the fittings has been established. Similarly, when the detent enters notch 132 the user will sense that the expanded spacing has been achieved. This detent arrangement may not be adopted as the length of the strap 16 and slot 82 as well as the width of the waists 96 may establish the maximum and minimum spacing for the fittings.

Having described this invention in detail, those skilled in the art will appreciate that numerous modifications may be made thereof without departing from its spirit. Therefore, it is not intended to limit the breadth of this invention to the single embodiment illustrated and described. Rather, it is intended that the scope of this invention be determined by the appended claims and their equivalents.

What is claimed is:

1. In a multi-channel pipetting system including a plurality of passages, each of said passages for transferring a liquid volume, means for drawing a liquid volume into each of said passages, and means for expelling each of the liquid volumes from each of said passages through a pipette tip in fluid communication therewith, wherein the improvement comprises
a housing for the pipetting system,
a slotted track in the housing,
a plurality of pipette tip fittings, with one tip fitting connected to each passage and slidably mounted on the track,
and means connected to each of the fittings for adjusting the distance between adjacent ones of said fittings on the track.

2. A pipetting system as set forth in claim 1, wherein said means for adjusting the distance between adjacent ones of said fittings includes means for simultaneously adjusting the distance between all of said fittings.

3. A pipetting system as set forth in claim 2, wherein said means for adjusting the distance between adjacent ones of the fittings includes
a flexible strap attached to each of said fittings to form an array of fittings;
an actuating rod attached to one end of said array for elongated said array by straightening the strap and shortening the array by folding the strap.

4. A pipetting system as set forth in claim 2, wherein said system has a stripper for removing pipette tips attached to each of said fittings.

5. A pipetting system as set forth in claim 6, wherein said stripper comprises:
a trigger mounted on the housing;
a spring attached to said trigger and biasing said trigger to a first position;
a stripper plate movably mounted in the housing;
and links attached between said trigger and stripper plate for actuating the plate to engage and force the pipette tips off the respective fittings.

6. A pipetting system as set forth in claim 5, wherein said stripper plate is slotted and each of the fittings extends through the slot.

7. A pipetting system as set forth in claim 6, wherein said stripper plate has stepped edges about the slot causing the plate to engage certain ones of the pipette tips in sequence when the trigger is actuated.

8. In a multi-channel pipetting system including a plurality of passages, each of said passages for transferring a liquid volume, means for drawing a liquid volume into each of said passages, and means for expelling each of the liquid volumes from each of said passages through a pipette tip in fluid communication therewith, wherein the improvement comprises
a housing for the pipetting system,
a slotted track in the housing,
a plurality of pipette tip fittings, with one tip fitting connected to each passage and slidably mounted on the track,
a flexible, non-stretchable strap attached to each of said fittings to form an array of fittings and
an actuating rod attached to an end of said array for elongating said array by straightening the strap and shortening the array by folding the strap.

9. A pipetting system as set forth in claim 8, wherein said rod has spaced notches,
and detent means are mounted in the housing for engaging said notches for securing said array in selected positions.

10. In a multi-channel pipetting system including a plurality of passages, each of said passages for transfering a liquid volume, means for drawing a liquid volume into each of said passages, and means for expelling each of the liquid volumes from each of said passages through a pipette tip in fluid communication therewith, wherein the improvement comprises a housing for the pipetting system having a plurality of fittings for holding disposable pipette tips with one tip fitting connected to each passage, support means on the housing for movably supporting each of the fittings, and slidable actuating means extending from the housing and connected to each of the fittings for manually moving said fittings between selected positions in order to vary the space between adjacent ones of said fittings.

11. A multi-channel pipetting system as defined in claim 10 wherein a stripper assembly is mounted on the housing adjacent the fittings for removing the pipette tips carried on the respective fittings.

12. A multi-channel pipetting system as defined in claim 11 wherein the stripper assembly remains adjacent to and is arranged for removing the pipette tips from the respective fittings regardless of the spacing between adjacent ones of the fittings.

13. A multi-channel pipetting system as defined in claim 11 wherein the housing has a hand gripping portion and a lower portion carrying the means for supporting each of the fittings.

14. A multi-channel pipetting system as defined in claim 13 wherein the means for supporting the fittings is mounted on the hand gripping portion and connected to the stripper assembly for actuating said assembly for removing the pipette tips.

15. A multi-channel pipetting system as defined in claim 14 wherein the actuating means for moving the fittings extends from the lower portion of the housing and is manually actuable.

16. A multi-channel pipetting system as defined in claim 10 wherein the actuating means supporting the fittings includes a slot in which the fittings are slidably supported, and a flexible strap having individual connections to each of said fittings which is foldable and interconnects the fittings enabling adjacent ones of the fittings to be separated by a maximum distance determined by the space between the connections of each of the fittings to the strap.

17. A multi-channel pipetting system as defined in claim 10 wherein the fittings are aligned in a row in the support means, and one of the two end fittings is held immovably in said support means.

18. In a multi-channel pipetting system including a plurality of passages, each of said passages for transfering a liquid volume, means for drawing a liquid volume into each of said passages, and means for expelling each of the liquid volumes from each of said passages through a pipette tip in fluid communication therewith, wherein the improvement comprises a housing for the pipetting system having a plurality of fittings for holding disposable pipette tips with one tip fitting connected to each passage, a support means on the housing for movably supporting each of the fittings, said fittings being aligned in a row in the support means to provide two end fittings and at least one intermediate fitting, a rod connected to the fittings for manually moving said fittings to uniformly vary the distance between adjacent ones of said fittings, one of the two end fittings being held immovably in the support means, and wherein said rod is connected to the other of the two end fittings.

19. In an adjustable multi-channel pipetting system including a plurality of passages, each of said passages for transfering a liquid volume; means for drawing a liquid volume into each of said passages; and means for expelling each of the liquid volumes from each of said passages through a pipette tip in fluid communication therewith, wherein the improvement comprises a housing for the pipetting system having a handle section and a lower section, said lower section having a bottom wall, a mounting plate in the lower section adjacent to the bottom wall, a plurality of pipette tip fittings, each tip fitting connected to a passage and each removably carrying a pipette tip and movably mounted in a row on the plate, each of said fittings extending out of the bottom wall of the lower section, means interconnecting the fittings enabling each fitting on the plate to move relative to the other fittings thereon so that the spacing between adjacent ones of said fittings may be varied, and an actuator secured to each of the fitting enabling the spacing between adjacent ones of the fittings to be uniformly changed.

20. An adjustable multi-channel pipetting system as defined in claim 19 wherein said actuator includes a rod extending out of the lower section beneath the handle section.

21. An adjustable multi-channel pipetting system as defined in claim 19 wherein a stripper is mounted on the lower section for removing the pipette tips from the respective fittings, and a trigger is mounted on the handle section and connected to the stripper for actuating the stripper.

22. An adjustable multi-channel pipetting system as defined in claim 19 wherein the means interconnecting each of the fittings is a flexible strap.

23. An adjustable multi-channel pipetting system as defined in claim 19 wherein the fitting at one end of the row is fixed and the fitting at the other end of the row is connected to the actuator.

* * * * *

UNITED STATES PATENT AND TRADEMARK OFFICE
CERTIFICATE OF CORRECTION

PATENT NO.  : 5,061,449

DATED       : October 29, 1991

INVENTOR(S) : EXPANDABLE MULTI-CHANNEL PIPETTER

It is certified that error appears in the above—identified patent and that said Letters Patent is hereby corrected as shown below:

In column 6, line 31, delete "6", and insert --4--.

Signed and Sealed this

Sixth Day of April, 1993

Attest:

STEPHEN G. KUNIN

*Attesting Officer*     Acting Commissioner of Patents and Trademarks